United States Patent [19]

Takahashi et al.

[11] Patent Number: 4,578,410
[45] Date of Patent: Mar. 25, 1986

[54] PIPERIDINE DERIVATIVES, THEIR PRODUCTION AND STABILIZED POLYMER COMPOSITIONS CONTAINING SAME

[75] Inventors: Yukoh Takahashi; Takeo Fujii, both of Toyonaka; Masahisa Shionoya, Izumi; Shinichi Yachigo, Toyonaka; Tamaki Ishii, Suita, all of Japan

[73] Assignee: Sumitomo Chemical Company, Limited, Osaka, Japan

[21] Appl. No.: 644,680

[22] Filed: Aug. 27, 1984

[30] Foreign Application Priority Data

Sep. 5, 1983 [JP] Japan ................................. 58-163734
May 10, 1984 [JP] Japan ................................. 59-94371
May 21, 1984 [JP] Japan ................................. 59-103362

[51] Int. Cl.$^4$ ............................................. C08K 5/34
[52] U.S. Cl. ..................................... 524/102; 546/17; 546/187
[58] Field of Search .................... 524/102; 546/17, 18, 546/187

[56] References Cited

U.S. PATENT DOCUMENTS 3,899,464  8/1975  Murayama et al. ................. 260/45.8
4,016,168  4/1977  Murayama et al. ................. 546/17
4,128,608  12/1978 Minagawa et al. ................. 211/244
4,287,337  9/1981  Guglielmetti et al. .............. 546/17

FOREIGN PATENT DOCUMENTS 27620   4/1981   European Pat. Off. .
119212  7/1974   Japan .
111138  3/1977   Japan .
155972  7/1978   Japan .
1336403 11/1973  United Kingdom .
1417835 12/1975  United Kingdom .

Primary Examiner—John Kight
Assistant Examiner—Kriellion Morgan
Attorney, Agent, or Firm—Wenderoth, Lind & Ponack

[57] ABSTRACT

There are provided piperidine derivatives having the formula

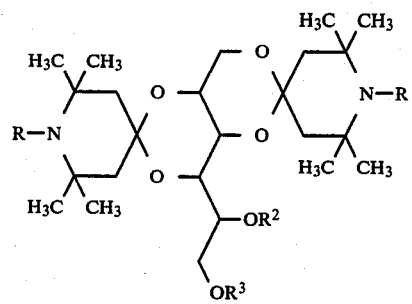

wherein R represents a hydrogen atom or a $C_1$-$C_3$ group, and $R^2$ and $R^3$ represent a hydrogen atom or taken together, form

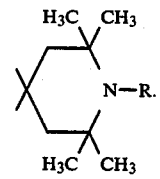

There is also provided a method for producing the above compounds which comprises reacting a tricetonamine derivative represented by the formula

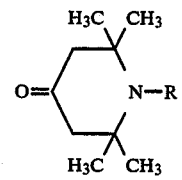

wherein R has the same meaning as described above, or its salt with sorbitol.

The subject piperdine derivatives are useful as stabilizers for preventing the deterioration of polymers by light.

20 Claims, No Drawings

PIPERIDINE DERIVATIVES, THEIR PRODUCTION AND STABILIZED POLYMER COMPOSITIONS CONTAINING SAME

The present invention relates to a piperidine derivative, its production and stabilized high polymer compositions containing it.

It is well known that high polymers such as polyethylene, polypropylene, polyvinyl chloride, polyurethane, ABS resin, etc. deteriorate by the action of light, thereby showing a remarkable reduction in mechanical property followed by phenomena such as softening, brittleness, surface crack, discoloration and the like.

For the purpose of preventing such deterioration by light, the use of various photostabilizers is well known. Such photostabilizers include for example benzophenone compounds [e.g. 2-hydroxy-4-n-octoxybenzophenone], benzotriazole compounds [e.g. 2-(2-hydroxy-3-tert-butyl-5-methylphenyl)-5-chlorobenzotriazole, 2-(2-hydroxy-3,5-dipentylphenyl)benzotriazole], cyanoacrylate compounds [e.g. ethyl 2-cyano-3,3-diphenylacrylate], Ni compounds [e.g. Ni salt of bis(3,5-di-tert-butyl-4-hydroxybenzylphosphoric acid monoethyl ester)], hindered piperidine compounds [e.g. 4-benzoyloxy-2,2,6,6-tetramethylpiperidine, bis(2,2,6,6-tetramethyl-4-piperidyl)sebacate, a reaction product of N,N'-bis(2,2,6,6-tetramethyl-4-piperidylhexylenediamine) with 2,4-dichloro-6-tert-octylamino-1,3,5-triazine], and the like.

These photostabilizers, however, are not quite satisfactory in terms of light fastness.

Also, it is well known that, for the purpose of preventing deterioration by heat and oxidation, phenol compounds and sulfur compounds are used together with these photostabilizers. But, when the hindered piperidine compound, which is a popular photostabilizer is used, there occurred a serious problem in that the excellent photostabilizing effect inherent to the compound is extremely reduced probably due to the antagonistic action of the compound to the sulfur stabilizer.

The present inventors extensively studied these problems and as a result, found that a piperidine derivative represented by the formula (I) described below has an excellent effect in preventing high polymers from deterioration by light, and further found that even when it is used together with sulfur compounds, it shows no such extreme reduction in light fastness as noticed in combination of the various popular hindered piperidine compounds with the sulfur compound. The present inventors thus completed the present invention.

An object of the present invention is to provide excellent photostabilizers represented by the formula (I),

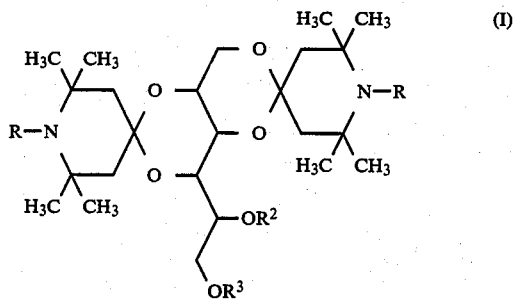

wherein R represents a hydrogen atom or a $C_1$–$C_3$ alkyl group, and $R^2$ and $R^3$ represents a hydrogen atom or taken together, form

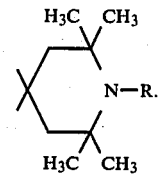

The piperidine derivative of the present invention represented by the foregoing formula (I) is a novel compound which was first synthesized by the present inventors, and it can be produced by reacting a triacetonamine derivative represented by the formula (II),

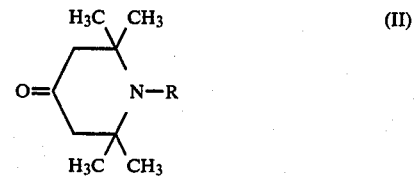

wherein R has the same meaning as described above, or its salt with sorbitol represented by the formula (III),

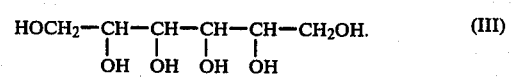

As the salt of the triacetonamine derivative, there are given salts with a mineral acid (e.g. hydrochloric acid, phosphoric acid, sulfuric acid), carboxylic acid (e.g. acetic acid, oxalic acid), sulfonic acid (e.g. p-toluenesulfonic acid) and the like.

Also, the $C_1$–$C_3$ alkyl group includes a methyl, ethyl, n-propyl and isopropyl groups and the like.

This reaction is carried out with or without a solvent in the presence of an acidic catalyst or dehydrating agent.

As the solvent used, there are given for example aliphatic hydrocarbons (e.g. hexane, heptane), aromatic hydrocarbons (e.g. benzene, toluene, xylene), alicyclic hydrocarbons (e.g. cyclohexane), water-soluble polar solvents (e.g. N,N-dimethylformamide, dimethyl sulfoxide, dioxane, sulfolane), alcohols (e.g. methanol, ethanol, propanol, isopropyl alcohol, butanol, tert-butanol, n-amyl alcohol, isoamyl alcohol, 2-ethylhexyl alcohol, cyclohexanol), glycol ethers (e.g. ethylene glycol monomethyl ether, ethylene glycol monoethyl ether, ethylene glycol monobutyl ether), and the like. These solvents may be used alone or in combinations of two or more of them.

The acidic catalyst includes for example hydrochloric acid, sulfuric acid, phosphoric acid, polyphosphoric acid, hydrobromic acid, p-toluenesulfonic acid, zinc chloride, boron trifluoride, cation-exchange resins, aluminum chloride/polymer complexes, selenium oxide, ammonium chloride and the like. The dehydrating agent includes calcium chloride, etc.

In this reaction of the triacetonamine derivative or its salt with sorbitol, when both $R^2$ and $R^3$ in the formula (I) are a hydrogen atom, the amount of said derivative or its salt used is generally 1.8 to 2.5 moles, preferably 1.8 to 2.2 moles based on 1 mole of sorbitol, and that of the acidic catalyst or dehydrating agent used is 0.01 to 4 moles, preferably 0.1 to 3 moles based on 1 mole of sorbitol. Also, when $R^2$ and $R^3$ in the formula (I), taken together, form

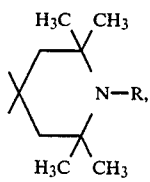

the amount of said derivative or its salt used is generally 2 to 6 moles, preferably 2.5 to 4 moles based on 1 mole of sorbitol, and that of the acidic catalyst or dehydrating agent used is 0.01 to 6 moles, preferably 0.1 to 4 moles based on 1 mole of sorbitol.

The reaction temperature is 10° to 300° C., preferably 60° to 200° C. After completion of the reaction, the objective compound can be isolated from the reaction mixture, for example, by making the reaction mixture alkaline, removing the solvent from the organic layer and if necessary, recrystallizing the product from a suitable solvent.

As the piperidine derivative of the present invention thus obtained, there are given for example 1,3:2,4:5,6-tris-O-(2,2,6,6-tetramethyl-4-piperidinylidene)sorbitol, 1,3:2,4:5,6-tris-O-(1,2,2,6,6-pentamethyl-4-piperidinylidene)sorbitol, 1,3:2,4:5,6-tris-O-(2,2,6,6-tetramethyl-1-propyl-4-piperidinylidene)sorbitol, 1,3:2,4-bis-O-(2,2,6,6-tetramethyl-4-piperidinylidene)sorbitol, 1,3:2,4-bis-O-(1,2,2,6,6-pentamethyl-4-piperidinylidene)sorbitol, 1,3:2,4-bis-O-(2,2,6,6-tetramethyl-1-propyl-4-piperidinylidene)sorbitol and the like. In the method of the present invention, however, depending upon its reaction condition, there sometimes occurs a case wherein the disubstituted product of sorbitol, i.e. a compound of the formula (I) in which both $R^2$ and $R^3$ are a hydrogen atom, and the trisubstituted product thereof, i.e. a compound of the formula (I) in which $R^2$ and $R^3$, taken together, for a hindered piperidine group, are produced at the same time, and therefore wherein the desired compound represented by the formula (I) is a mixture of these disubstituted product and trisubstituted one. But, when said desired compound is used as a stabilizer, etc., this mixture may be used as such without special problems.

When the piperidine derivative of the present invention is used as a stabilizer for high polymers, its amount blended with the high polymer is generally 0.01 to 5 parts by weight, preferably 0.05 to 2 parts by weight based on 100 parts by weight of said high polymer. For blending them, the well-known apparatus and methods for incorporating stabilizers, pigments, fillers, etc. in synthetic high polymers may be used almost as such.

In applying the piperidine derivative of the present invention as a stabilizer for high polymers, other additives such as antioxidants, photostabilizers, metal deactivating agents, metal soaps, nucleating agents, lubricants, antistatic agents, flame retardants, pigments, fillers and the like may be used together with said piperidine derivative.

Particularly, the thermal stability and oxidation stability of high polymers can be improved by using a phenol antioxidant together. This phenol antioxidant includes for example 2,6-di-tert-butyl-4-methylphenol, n-octadecyl 3-(3,5-di-tert-butyl-4-hydroxyphenyl)propionate, 2,2'-methylenebis(4-methyl-6-tert-butylphenol), 4,4'-butylidenebis(3-methyl-6-tert-butylphenol), 4,4'-thiobis(3-methyl-6-tert-butylphenol), 2-tert-butyl-6-(3-tert-butyl-5-methyl-2-hydroxybenzyl)-4-methylphenyl acrylate, 1,1,3-tris(2-methyl-4-hydroxy-5-tert-butylphenyl)butane, 1,3,5-trimethyl-2,4,6-tris(3-alkyl-5-tert-butyl-4-hydroxybenzyl)benzene, 1,3,5-tris(3-alkyl-5-tert-butyl-4-hydroxybenzyl)isocyanurate, 1,3,5-tris[3-(3-alkyl-5-tert-butyl-4-hydroxyphenyl)propionyloxyethyl]isocyanulate, ethylene glycol bis[3,3-bis(4-hydroxy-3-tert-butylphenyl)butanate], pentaerythritol tetrakis[3-(3-alkyl-5-tert-butyl-4-hydroxyphenyl)propionate] and the like.

Also, sulfur antioxidants such as dilauryl thiodipropionate, dimyristyl thiodipropionate, distearyl thiodipropionate, pentaerythritol tetrakis(3-dodecylthiopropionate), 3,9-bis(2-dodeceylthioethyl)-2,4,8,10-tetraoxaspiro[5.5]undecane and the like may be used together.

When the piperidine derivative of the present invention is used together with the phenol antioxidant and sulfur antioxidant, the weight ratio of the piperidine derivative to the phenol antioxidant to the sulfur antioxidant is 1–20 to 1 to 1–15, and the total weight of these stabilizers is generally 0.01 to 5 parts by weight, preferably 0.05 to 2 parts by weight based on 100 parts by weight of a high polymer.

Also, the color of high polymers can be improved by using a phosphite antioxidant.

The phosphite antioxidant includes for example tris(nonylphenyl)phosphite, distearyl pentaerythritol diphosphite, tris(2,4-di-tert-butylphenyl)phosphite, tris(2-tert-butyl-4-methylphenyl)phosphite, bis(2,4-di-tert-butylphenyl)pentaerythritol diphosphite, tetrakis(2,4-di-tert-butylphenyl)-4,4'-biphenylene diphosphonite and the like.

Also, the light fastness of high polymers can be further improved by adding photostabilizers other than the hindered piperidine compounds.

As such photostabilizers, there are given for example benzophenone compounds such as 2-hydroxy-4-methoxybenzophenone, 2-hydroxy-n-octoxybenzophenone, 2,2'-dihydroxy-4,4'-dimethoxybenzophenone, etc., benzotriazole compounds such as 2-(2-hydroxy-3-tert-butyl-5-methylphenyl)-5-chlorobenzotriazole, 2-(2-hydroxy-3,5-dipentylphenyl)benzotriazole, 2-(2-hydroxy-3-tert-butyl-5-methylphenyl)benzotriazole, 2-(2-hydroxy-5-methylphenyl)benzotriazole, 2-(2-hydroxy-3,5-di-tert-butylphenyl)benzotriazole, 2-(2-hydroxy-3,5-di-tert-butylphenyl)-5-chlorobenzotriazole, 2-(2-hydroxy-5-tert-octylphenyl)benzotriazole, 2-[2-hydroxy-3,5-di-(α,α-dimethylbenzyl)phenyl]benzotriazole, etc., benzoate compounds such as phenyl salicylate, p-tert-butylphenyl salicylate, 2,4-di-tert-butylphenyl 3',5'-di-tert-butyl-4'-hydroxybenzoate, hexadecyl 3,5-di-tert-butyl-4-hydroxybenzoate, etc., nickel compounds such as Ni salt of dibutyldithiocarbamic acid, [2,2'-thiobis(4-tert-octylphenolate)]-n-butylamine nickel complex, Ni salt of bis(3,5-di-tert-butyl-4-hydroxybenzylphosphoric acid monoethyl ester), etc., cyanoacrylate compounds such as ethyl 2-cyano-3,3-diphenylacrylate, etc., and oxalic acid diamides such as N-2-ethylphenyl-N'-2-ethoxy-5-tert-butylphenyloxalic acid diamide, N-2-ethylphenyl-N'-2-ethoxyphenyloxalic acid diamide, etc.

As high polymers stabilized by the piperidine derivative of the present invention, there are given for example polyα-olefins such as low-density polyethylene, medium- and high-density polyethylenes, linear low-density polyethylene, polypropylene, polybutene-1, etc., polyα-olefin copolymers such as propylene/ethylene random or block copolymers, ethylene/butene-1 random copolymers, etc., polyα-olefin/vinyl monomer copolymers such as maleic acid anhydride-modified polypropylene, etc., mixtures thereof, chlorinated polyethylene, EVA resin, polyvinyl chloride, methacrylic resin, polystyrene, high impact polystyrene, ABS resin, AES resin, MBS resin, polyethylene terephthalate, polybutylene terephthalate, polyamide, polyimide, polycarbonate, polyacetal, polyurethane, unsaturated polyester resin, and besides rubbers such as isoprene rubber, butadiene rubber, acrylonitrile/butadiene copolymer rubber, styrene/butadiene copolymer rubber, etc., and blends of these resins.

Next, the present invention will be illustrated in detail with reference to the following examples, which are not however to be interpreted as limiting the invention thereto.

EXAMPLE 1

To a four-necked flask equipped with a thermometer, a stirrer and Dean-Stark trap were added 100 g (0.52 mole) of triacetonamine hydrochloride, 20.94 g (0.12 mole) of sorbitol, 300 g of toluene and 100.8 g of p-tolunesulfonic acid monohydrate, and the mixture was heated with stirring and reacted at 110° to 120° C. for 3 hours.

During this period, formed water was removed from the reaction system by means of the Dean-Stark trap.

After completion of the reaction, an aqueous sodium hydroxide solution was added to the reaction solution to make the product soluble in toluene. The toluene layer containing the dissolved product was separated, washed with water and dried, and toluene was removed by evaporation to obtain 51.89 g of a yellowish brown and glassy 1,3:2,4:5,6-tris-O-(2,2,6,6-tetramethyl-4-piperidinylidene)sorbitol (yield, 73% based on sorbitol).

This yellowish brown and glassy product was recrystallized from a hexane/water mixture to obtain 25.92 g of a white crystal (m.p., 43°–46° C.).

FD-mass spectrometry:

A parent ion peak 593 was confirmed.

$^1$H-NMR (CDCl$_3$, D$_2$O): δ(ppm) 1.22(36H, s), 1.55(12H, m), 4.05(8H, m)

$^{13}$C-NMR: δ(ppM) 31.106 (off resonance, q), 31.261 (q), 31.839 (q), 32.058 (q), 32.220 (q), 32.315 (q), 32.379 (q), 32.681 (q), 32.900 (q), 44.753 (t), 45.342 (t), 45.968 (t), 46.388 (t), 46.614 (t), 46.921 (t), 51.342 (s), 65.309 (t), 67.386 (t), 74.666 (d), 76.656 (d), 77.717 (d), 79.238 (d), 110.031 (s), 110.273 (s), 110.477 (s).

EXAMPLE 2

To the same flask as used in Example 1 were added 94.1 g (0.6 mole) of triacetonamine, 36.4 g (0.2 mole) of sorbitol, 500 g of xylene and 149.5 g of p-toluenesulfonic acid monohydrate, and the mixture was reacted at 135° to 140° C. for 4 hours.

After completion of the reaction, after-treatment and purification were carried out in the same manner as in Example 1 to obtain 73.2 g of a yellowish brown and glassy 1,3:2,4:5,6-tris-O-(2,2,6,6-tetramethyl-4-piperidinylidene)sorbitol (yield, 62% based on sorbitol).

This product was recrystallized from a hexane/water mixture to obtain 61.7 g of a white crystal (yield, 52% based on sorbitol).

From the results of melting point, elementary analysis and $^1$H-NMR, it was confirmed that this crystal was the same compound as obtained in Example 1.

EXAMPLE 3

To the same flask as used in Example 1 were added 102.4 g (0.6 mole) of 1,2,2,6,6-pentamethyl-4-piperidone, 36.4 g (0.2 mole) of sorbitol, 500 g of xylene and 123.6 g of p-toluenesulfonic acid monohydrate, and the mixture was reacted and after-treated in the same manner as in Example 2 to obtain 87.8 g of 1,3:2,4:5,6-tris-O-(1,2,2,6,6-pentamethyl-4-piperidinylidene)sorbitol as a pale yellow and viscous liquid (yield, 69% based on sorbitol).

FD-mass spectrometry:

A parent ion peak 635 was confirmed.

$^1$H-NMR (CDCl$_3$, 60 MHz) δ(ppm) 1.15(36H, s), 1.54(12H, m), 2.24(9H, s), 4.04(8H, m)

EXAMPLE 4

To a four-necked flask equipped with a thermometer, a stirrer and a condenser were added 100 g (0.52 mole) of triacetonamine hydrochloride, 45.5 g (0.25 mole) of sorbitol and 300 g of toluene, and thereafter, 100.8 g of p-toluenesulfonic acid monohydrate was added with stirring. The mixture was heated to 110° C. and reacted at this temperature for 1 hour.

After completion of the reaction, an aqueous sodium hydroxide solution was added to the reaction solution to make the product soluble in toluene. The toluene layer containing the dissolved product was separated, washed with water and dried, and toluene was removed by evaporation to obtain 71 g of 1,3:2,4-bis-O-(2,2,6,6-tetramethyl-4-piperidinylidene)sorbitol as a yellow crystal (yield, 62.3% based on sorbitol).

This yellow crystal was dissolved in toluene and treated with activated carbon to obtain a pale yellow crystal. m.p., 167°–173° C.

A parent ion peak 456 was confirmed by FD-MS.

$^1$H-NMR (DMSO, D$_2$O, TSP): δ(ppm) 1.16(24H, s), 1.53(8H, s), 3.66(5H, d), 4.00(3H, s)

EXAMPLE 5

To the same flask as used in Example 1 were added 80.7 g (0.52 mole) of triacetonamine, 45.5 g (0.25 mole) of sorbitol and 300 g of toluene, and thereafter, 100.8 g of p-toluenesulfonic acid monohydrate was added with stirring. The mixture was heated to 110° C. and reacted at this temperature for 1 hour.

After completion of the reaction, the reaction solution was after-treated in the same manner as in Example 1 to obtain 68 g of 1,3:2,4-bis-O-(2,2,6,6-tetramethyl-4-piperidinylidene)sorbitol as a yellow crystal (yield, 60% based on sorbitol). The physical property of this product was the same as that of the product obtained in Example 4.

EXAMPLE 6

To the same flask as used in Example 1 were added 102.4 g (0.6 mole) of 1,2,2,6,6-pentamethyl-4-piperidone, 54.7 g (0.3 mole) of sorbitol and 300 g of xylene, and thereafter, 116.0 g of p-toluenesulfonic acid monohydrate was added with stirring. The mixture was heated to 120° C. and reacted at this temperature for 1 hour.

After completion of the reaction, after-treatment and purification were carried out in the same manner as in Example 1 to obtain 110.4 g of a pale yellow and oily 1,3:2,4-bis-O-(1,2,2,6,6-pentamethyl-4-piperidinylidene)sorbitol (yield, 76% based on sorbitol).
M+1 (485) was confirmed by FD-MS.
$^1$H-NMR (DMSO, D$_2$O, TSP): δ(ppm) 1.11(24H, s), 1.52(8H, s), 2.22(6H, s), 3.63(5H, d), 4.03(3H, s)

| Elementary analysis (for C$_{26}$H$_{48}$N$_2$O$_6$): | | |
|---|---|---|
| | Found | Calculated |
| C | 64.00% | 64.43% |
| H | 9.72% | 9.98% |
| N | 5.00% | 5.78% |

EXAMPLE 7

The following blend was mixed on a mixer for 5 minutes and then melt-kneaded at 180° C. on a mixing roll to obtain a compound. This compound was then formed into a sheet of 1 mm in thickness on a hot press kept at 210° C. to prepare a test piece of 150×30×1 mm in size.

This test piece was exposed to light in a Sunshine weather-O-meter (light source, carbon arc; temperature of black panel, 83±3° C.; spraying cycle, 120 minutes; spraying time, 18 minutes) and folded as a lobster every 60 hours to obtain a time required for the test piece to break into two. The weathering resistance was evaluated by this time.

The result is shown in Table 1.

| Compounding: | Part by weight |
|---|---|
| Unstabilized polypropylene | 100 |
| Calcium stearate | 0.1 |
| 2,6-Di-tert-butyl-4-methylphenol | 0.05 |
| Test compound | 0.2 |

In the table, UVA-1 to UVA-9 and I-1 to I-4 show the following compounds:

UVA-1: 2-Hydroxy-4-methoxybenzophenone
UVA-2: 2-Hydroxy-4-n-octoxybenzophenone
UVA-3: 2-(2-Hydroxy-5-methylphenyl)benzotriazole
UVA-4: 2-(2-Hydroxy-3-tert-butyl-5-methylphenyl)-5-chlorobenzotriazole
UVA-5: 2-(2-Hydroxy-3,5-dipentylphenyl)benzotriazole
UVA-6: Ethyl 2-cyano-3,3′-diphenylacrylate
UVA-7: Nickel salt of bis(3,5-di-tert-butyl-4-hydroxybenzylphosphoric acid) monoethyl ester
UVA-8: Bis(2,2,6,6-tetramethyl-4-piperidyl)sebacate
UVA-9: Bis-O-(2,2,6,6-tetramethyl-4-piperidinylidene)-pentaerythritol
I-1: 1,3:2,4:5,6-Tris-O-(2,2,6,6-tetramethyl-4-piperidinylidene)sorbitol
I-2: 1,3:2,4:5,6-Tris-O-(1,2,2,6,6-pentamethyl-4-piperidinylidene)sorbitol
I-3: 1,3:2,4-Bis-O-(2,2,6,6-tetramethyl-4-piperidinylidene)sorbitol
I-4: 1,3:2,4-Bis-O-(1,2,2,6,6-pentamethyl-4-piperidinylidene)sorbitol

TABLE 1

| | No. | Test compound | Weathering resistance (hour) |
|---|---|---|---|
| Example | 1 | I-1 | 2120 |
| | 2 | I-2 | 2050 |
| | 3 | I-3 | 2100 |
| | 4 | I-4 | 2040 |
| Comparative | 5 | UVA-1 | 180 |

TABLE 1-continued

| | No. | Test compound | Weathering resistance (hour) |
|---|---|---|---|
| example | 6 | UVA-2 | 420 |
| | 7 | UVA-3 | 240 |
| | 8 | UVA-4 | 600 |
| | 9 | UVA-5 | 420 |
| | 10 | UVA-6 | 240 |
| | 11 | UVA-7 | 360 |
| | 12 | UVA-8 | 1800 |
| | 13 | UVA-9 | 1680 |
| | 14 | No addition | 120 |

EXAMPLE 8

To a 25% urethane dope (comprising 25 parts of a polyurethane resin, 3.75 parts of dimethylformamide and 71.25 parts of tetrahydrofuran) was added each of the test compounds shown in Table 2 at a rate of 1 wt.% based on the above polyurethane resin. The mixture was coated onto polyester film in a thickness of 1.2 mm and dried for 1 hour in a dryer kept at 45° C. The sheet thus obtained was punched into No. 3 dumbbell test pieces. The test pieces were exposed to light for 60 hours and 120 hours in a fade-O-meter (light source, ultraviolet carbon arc; temperature of black panel, 63±3° C.), and a percent retention of break strength was obtained by the tensile test (tensile rate, 200 mm/mm; measurement temperature, 25° C.).

The result is shown in Table 2.

TABLE 2

| | | | Percent retention of break strength | |
|---|---|---|---|---|
| | No. | Test compound | 60 hr | 120 hr |
| Example | 1 | I-1 | 80 | 58 |
| | 2 | I-2 | 78 | 56 |
| | 3 | I-3 | 79 | 58 |
| | 4 | I-4 | 77 | 55 |
| Comparative | 5 | UVA-2 | 43 | 22 |
| example | 6 | UVA-5 | 56 | 30 |
| | 7 | UVA-8 | 66 | 40 |
| | 8 | No addition | 30 | 16 |

EXAMPLE 9

The blend described below was melt-kneaded on a mixing roll kept at 150° C. and then formed into a sheet of 0.5 mm in thickness on a hot press kept at 160° C.

This sheet was exposed to light for 1200 hours in Sunshine weather-O-meter (light source, carbon arc; temperature of black panel, 63±3° C.; spraying cycle, 120 minutes; spraying time, 18 minutes), and the degree of discoloration was observed.

The result is shown in Table 3.

| Compounding: | Part by weight |
|---|---|
| Polyvinyl chloride | 100 |
| Dioctyl phthalate | 38 |
| Epoxidized soybean oil | 2 |
| Barium stearate | 1 |
| Zinc stearate | 0.3 |
| Test compound | 0.2 |

TABLE 3

| | No. | Test compound | Color |
|---|---|---|---|
| Example | 1 | I-1 | Pale yellow |
| | 2 | I-2 | Pale yellow |
| | 3 | I-3 | Pale yellow |

TABLE 3-continued

|  | No. | Test compound | Color |
|---|---|---|---|
|  | 4 | I-4 | Pale yellow |
| Comparative | 5 | UVA-2 | Brown spot |
| example | 6 | UVA-3 | Yellow |
|  | 7 | UVA-8 | Yellow |
|  | 8 | No addition | Blackish brown |

EXAMPLE 10

The following blend was mixed on a mixer for 5 minutes and then melt-kneaded at 180° C. on a mixing roll to obtain a compound. This compound was then formed into a sheet of 1 mm in thickness on a hot press kept at 210° C. to prepare a test piece of 150×30×1 mm in size.

This test piece was exposed to light in a Sunshine weather-O-meter (light source, carbon arc; temperature of black panel, 83±3° C.; spraying cycle, 120 minutes; spraying time, 18 minutes) and folded as a lobster every 60 hours to obtain a time required for the test piece to break into two. The weathering resistance was evaluated by this time.

Separately from this, a test piece of 40×40×1 mm in size was prepared, placed in a Geer oven kept at 160° C. and measured for a period of time required for 30% of its area to become brittle. This period of time was taken as a thermal brittleness induction period and used for evaluation of the thermal and oxidation stability.

The result is shown in Table 4.

| Compounding: | Part by weight |
|---|---|
| Unstabilized polypropylene | 100 |
| Calcium stearate | 0.1 |
| 2,6-Di-tert-butyl-4-methylphenol | 0.05 |
| Test compound { photostabilizer | 0.2 |
| phenol compound | 0.05 |
| sulfur compound | 0.25 |

In the table, UVA-10 and AO-1 to AO-3 show the following compounds:
UVA-10: Tinuvin 944 (produced by Ciba-Geigy Co.) (hindered piperidine photostabilizer)
AO-1: Tris(3,5-di-tert-butyl-4-hydroxybenzyl)isocyanurate
AO-2: Dilauryl 3,3'-thiodipropionate
AO-3: Pentaerythritol tetrakis(3-dodecylthiopropionate)

TABLE 4

|  | No. | Photo-stabilizer | Phenol compound | Sulfur compound | Light fastness (hour) | Thermal brittleness induction period (hour) |
|---|---|---|---|---|---|---|
| Example | 1 | I-1 | AO-1 | AO-2 | 1860 | 710 |
|  | 2 | I-2 | " | " | 1800 | 685 |
|  | 3 | I-3 | " | " | 1800 | 680 |
|  | 4 | I-4 | " | " | 1740 | 670 |
|  | 5 | I-1 | " | AO-3 | 1860 | 690 |
|  | 6 | I-2 | " | " | 1800 | 660 |
|  | 7 | I-3 | " | " | 1800 | 660 |
|  | 8 | I-4 | " | " | 1740 | 650 |
| Comparative example | 9 | UVA-2 | " | AO-2 | 480 | 490 |
|  | 10 | UVA-4 | " | " | 720 | 500 |
|  | 11 | UVA-5 | " | " | 480 | 490 |
|  | 12 | UVA-6 | " | " | 240 | 480 |
|  | 13 | UVA-7 | " | " | 240 | 485 |
|  | 14 | UVA-8 | " | " | 960 | 485 |
|  | 15 | UVA-10 | " | " | 900 | 480 |
|  | 16 | UVA-9 | " | " | 900 | 485 |
|  | 17 | UVA-2 | " | AO-3 | 480 | 480 |
|  | 18 | UVA-4 | " | " | 680 | 480 |
|  | 19 | UVA-5 | " | " | 420 | 480 |
|  | 20 | UVA-6 | " | " | 240 | 470 |
|  | 21 | UVA-7 | " | " | 420 | 475 |
|  | 22 | UVA-8 | " | " | 900 | 475 |
|  | 23 | UVA-10 | " | " | 840 | 470 |
|  | 24 | UVA-9 | " | " | 840 | 475 |
|  | 25 | UVA-4 | — | — | 600 | 45 |
|  | 26 | UVA-5 | — | — | 420 | 30 |
|  | 27 | UVA-6 | — | — | 240 | 20 |
|  | 28 | UVA-7 | — | — | 360 | 30 |
|  | 29 | UVA-8 | — | — | 1800 | 30 |
|  | 30 | UVA-10 | — | — | 1680 | 30 |
|  | 31 | UVA-9 | — | — | 1680 | 30 |
|  | 32 | I-1 | — | — | 2160 | 60 |
|  | 33 | I-2 | — | — | 2100 | 55 |
|  | 34 | I-3 | — | — | 2100 | 55 |
|  | 35 | I-4 | — | — | 2040 | 55 |
|  | 36 | — | AO-1 | AO-2 | 120 | 450 |
|  | 37 | — | " | AO-3 | 120 | 430 |
|  | 38 | No addition |  |  | 120 | 5 |

EXAMPLE 11

To a 25% urethane dope (comprising 25 parts of a polyurethane resin, 3.75 parts of dimethylformamide and 71.25 parts of tetrahydrofuran) was added each of the test compounds of the composition described below at a rate of 1% based on the above polyurethane resin. The mixture was coated onto polyester film in a thickness of 1.2 mm and dried for 1 hour in a dryer kept at 45° C. The sheet thus obtained was punched into No. 3 dumb-bell test pieces. The test pieces were exposed to light for 60 hours and 120 hours in a fade-O-meter (light source, ultraviolet carbon arc; temperature of black panel, 63±3° C.), and a percent retention of break strength was obtained by the tensile test (tensile rate, 200 mm/mm; measurement temperature, 25° C.).

The result is shown in Table 5.

| Test compound | { photostabilizer | 0.7 part |
|---|---|---|
|  | phenol compound | 0.05 part |
|  | sulfur compound | 0.25 part |

TABLE 5

|  | No. | Photo-stabilizer | Phenol compound | Sulfur compound | Percent retention of break strength 60 hr | 120 hr |
|---|---|---|---|---|---|---|
| Example | 1 | I-1 | AO-1 | AO-2 | 76 | 55 |
|  | 2 | I-2 | " | " | 74 | 53 |
|  | 3 | I-3 | " | " | 75 | 55 |
|  | 4 | I-4 | " | " | 73 | 52 |
| Comparative example | 5 | UVA-2 | " | " | 41 | 21 |
|  | 6 | UVA-5 | " | " | 53 | 28 |
|  | 7 | UVA-8 | " | " | 56 | 33 |
|  | 8 | — | " | " | 35 | 18 |
|  | 9 | No addition |  |  | 30 | 16 |

What is claimed is:
1. A piperidine derivative represented by the formula (I),

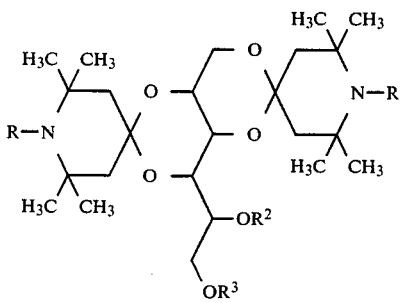

wherein R represents a hydrogen atom or a $C_1$–$C_3$ alkyl group, and $R^2$ and $R^3$ represent a hydrogen atom or taken together, form

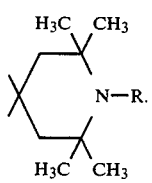

2. The piperidine derivative as described in claim 1, wherein R is a hydrogen atom.

3. The piperidine derivative as described in claim 1, wherein R is a methyl group.

4. The method for producing a piperidine derivative represented by the formula (I),

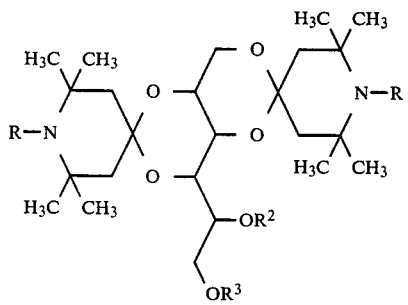

wherein R represents a hydrogen atom or a $C_1$–$C_3$ alkyl group, and $R^2$ and $R^3$ represent a hydrogen atom or taken together, form

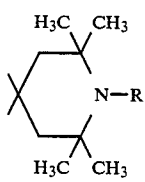

(in which R has the same meaning as described above), which comprises reacting a triacetonamine derivative represented by the formula (II),

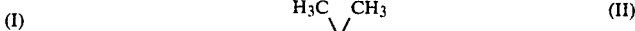

wherein R has the same meaning as described above, or its salt with sorbitol, with or without a solvent and in the presence of an acidic catalyst or dehydrating agent wherein the reaction temperature is 10° to 300° C.

5. The method as described in claim 4, wherein one or more members selected from the group consisting of aromatic hydrocarbons, aliphatic hydrocarbons, alicyclic hydrocarbons, water-soluble polar solvents, alcohols and glycol ethers are used as the solvent.

6. The method as described in claim 4, wherein one or more members selected from the group consisting of hydrochloric acid, sulfuric acid, phosphoric acid, polyphosphoric acid, hydrobromic acid, p-toluenesulfonic acid, zinc chloride, boron trifluoride, cation-exchange resins, aluminum chloride/polymer complexes, selenium oxide and ammonium chloride are used as the acidic catalyst.

7. The method as described in claim 4, wherein the amount of the compound of the formula (II) used is 1.8 to 2.5 moles based on 1 mole of sorbitol and that of the acidic catalyst used is 0.01 to 4 moles based on 1 mole of the same and wherein $R^2$ and $R^3$ both represent hydrogen atoms.

8. The method as described in claim 4, wherein the amount of the compound of the formula (II) used is 2 to 6 moles based on 1 mole of sorbitol and that of the acidic catalyst used is 0.01 to 6 moles based on 1 mole of the same and wherein $R^2$ and $R^3$ together represent

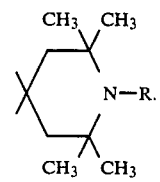

9. The method as described in claim 4, wherein the reaction temperature is 60° to 200° C.

10. A stabilized high polymer composition comprising a high polymer and 0.01 to 5 parts by weight of said polymer of at least one member selected from the piperidine derivatives represented by the formula (I),

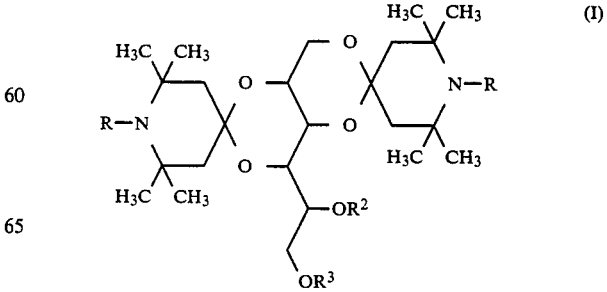

wherein R represents a hydrogen atom or a $C_1$–$C_3$ alkyl group, and $R^2$ and $R^3$ represent a hydrogen atom or taken together, form

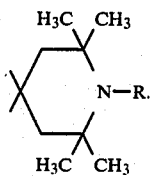

11. The stabilized high polymer composition as described in claim 10 wherein the composition further contains a phenolic antioxidant and a sulfur-containing antioxidant.

12. The stabilized high polymer composition as described in claim 11, wherein the weight ratio of the piperidine derivative represented by the formula (I) to the phenolic antioxidant to the sulfur-containing antioxidant is 1–20 to 1 to 1–15, and the total weight of the piperidine derivative (I), phenolic antioxidant and sulfur-containing antioxidant is 0.01 to 5 parts by weight based on 100 parts by weight of the high polymer.

13. The stabilized high polymer composition as described in claim 10, wherein R of the formula (I) is a hydrogen atom.

14. The stabilized high polymer composition as described in claim 10, wherein R of the formula (I) is a methyl group.

15. The stabilized high polymer composition as described in claim 11, wherein the hindered phenolic antioxidant is a hindered phenol.

16. The stabilized high polymer composition as described in claim 15, wherein the phenol antioxidant is 2,6-di-tert-butyl-4-methylphenol and/or tris(3,5-di-tert-butyl-4-hydroxybenzyl)isocyanurate.

17. The stabilized high polymer composition as described in claim 11, wherein the sulfur-containing antioxidant is dilauryl thiodipropionate, dimyristyl thiodipropionate, distearyl thiodipropionate or pentaerythritol tetrakis(3-dodecylthiopropionate).

18. The stabilized high polymer composition as described in claim 10, wherein the high polymer is polyolefin.

19. The stabilized high polymer composition as described in claim 10, wherein the high polymer is polyurethane.

20. The stabilized high polymer composition as described in claim 10, wherein the high polymer is polyvinyl chloride.

* * * * *